(12) United States Patent
Kankan et al.

(10) Patent No.: US 7,538,249 B2
(45) Date of Patent: May 26, 2009

(54) TOLTERODINE, COMPOSITIONS AND USES THEREOF, AND PREPARATION OF THE SAME

(75) Inventors: Rajendra Narayanrao Kankan, Maharashtra (IN); Dharmaraj Ramachandra Rao, Maharashtra (IN)

(73) Assignee: Cipla Limited, Maharashtra (IN)

( * ) Notice: Subject to any disclaimer, the term of this patent is extended or adjusted under 35 U.S.C. 154(b) by 47 days.

(21) Appl. No.: 10/596,767

(22) PCT Filed: Dec. 23, 2004

(86) PCT No.: PCT/GB2004/005420

§ 371 (c)(1),
(2), (4) Date: Dec. 18, 2006

(87) PCT Pub. No.: WO2005/061432

PCT Pub. Date: Jul. 7, 2005

(65) Prior Publication Data

US 2007/0142479 A1    Jun. 21, 2007

(30) Foreign Application Priority Data

Dec. 24, 2003 (GB) ................................. 0330056.3
Oct. 20, 2004 (GB) ................................. 0423300.3

(51) Int. Cl.
C07C 211/27 (2006.01)
C07C 43/205 (2006.01)
C07C 39/12 (2006.01)
A61K 31/135 (2006.01)

(52) U.S. Cl. ........................ 564/316; 568/640; 568/744; 514/648

(58) Field of Classification Search ........................ None
See application file for complete search history.

(56) References Cited

U.S. PATENT DOCUMENTS 5,382,600 A  1/1995  Jönsson et al.
5,922,914 A  7/1999  Gage et al.
7,005,449 B2  2/2006  Hawley et al.

FOREIGN PATENT DOCUMENTS

CN           1364757 A      8/2002
WO    WO 03/035599 A1       5/2003

OTHER PUBLICATIONS

Database CAPLUS on STN, Acc. No. 1990:55211, Joensson et al., EP325571 A1 (Jul. 26, 1989) (abstract).*
Database CAPLUS on STN, Acc. No. 2004:3735, Wu et al., CN1364757 (Aug. 21, 2002) (abstract).*
Database CASREACT on STN, Acc. No. 140:27656, CN 1364757 (Aug. 21, 2002) (abstract).*
International Search Report, PCT/GB2004/005420, May 25, 2005, 5 pgs.
International Preliminary Report on Patentability, PCT/GB2004/005420, Mar. 14, 2006, 6 pgs.
Keese, R., et al., "Crystallisation," Fundamentals of Preparative Organic Chemistry, The British Library, 1982, pp. 18-24.
Greene, Theodora W., et al., "Protective Groups in Organic Synthesis," John Wiley & Sons, Inc., Second Addition, 1991, 9 pgs.
Anderrson, Pher G., et al., "Asymmetric Total Synthesis of (+)-Tolterodine, a New Muscarinic Receptor Antagonist, via Copper-Assisted Asymmetric Conjugate Addition of Aryl Grignard Reagents to 3-Phenyl-prop-2-enoly-oxazolidinones," XP-001037685, Journal of Organic Chemistry, American Chemical Society, vol. 63, No. 22, 1998, pp. 8067-8070.

* cited by examiner

*Primary Examiner*—Brian J Davis
(74) *Attorney, Agent, or Firm*—Conley Rose, P.C.; Rodney B. Carroll

(57) ABSTRACT

Racemic tolterodine free base in crystalline form, tolterodine with improved purity, compositions and uses thereof, and processes of preparing the same.

24 Claims, No Drawings

TOLTERODINE, COMPOSITIONS AND USES THEREOF, AND PREPARATION OF THE SAME

CROSS-REFERENCE TO RELATED APPLICATIONS

This application is a filing under 35 U.S.C. 371 of International Application No. PCT/GIB2004/005420 filed Dec. 23, 2004, entitled "Tolterodine, Compositions and Uses Thereof, and Preparation of the Same," claiming priority of Great Britain Patent Application Nos. GB0330056.3 filed Dec. 24, 2003 and GB0423300.3 filed Oct. 20, 2004, which applications are incorporated by reference herein in their entirety.

FIELD OF THE INVENTION

The present invention is concerned with tolterodine, compositions and uses thereof, and processes of preparing the same.

BACKGROUND OF THE INVENTION

Tolterodine, (+)-N,N-diisopropyl-3-(2-hydroxy-5-methylphenyl)-3-phenylpropyl-amine, has the following structural formula (I)

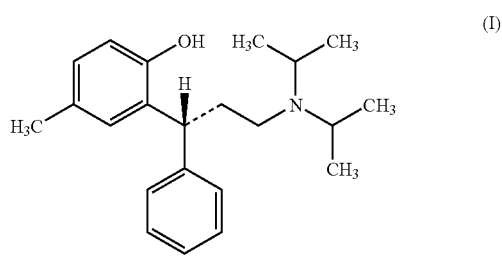

Tolterodine is an anti-cholinergic agent and is known to be particularly useful in the treatment of urinary incontinence. The preparation of tolterodine is described in U.S. Pat. No. 5,382,600, where the following reaction scheme is followed.

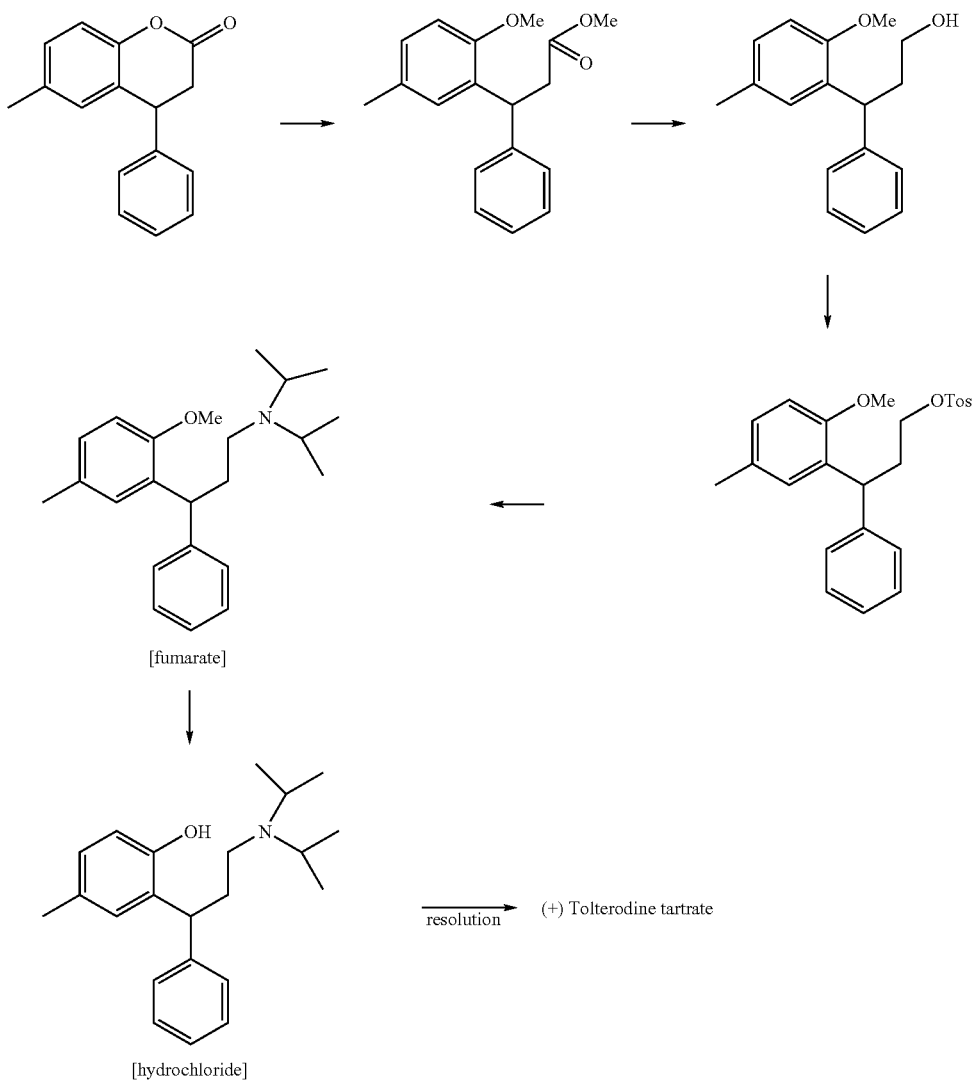

Deprotection by removal of hydroxy protecting groups is achieved according to U.S. Pat. No. 5,382,600 by treatment with hydrobromic acid, borontribromide or by catalytic hydrogenation. In the case where deprotection is carried out in the presence of pyridine hydrochloride, such deprotection is carried out at high temperature (greater than 200° C.) and in the absence of a solvent. The reaction mass obtained is highly viscous and requires quenching to about 80-90° C. before the addition of water. Using such techniques, it has been found that at 100° C., a hard mass which cannot be stirred is obtained and which subsequently cannot be quenched.

A further problem associated with prior art preparation techniques is that dimeric impurities are generally associated with tolterodine tartate prepared thereby, typically at a level of approximately 0.15-2%. Typical impurities can be 2-(3-{[3-(2-hydroxy,5-methyl-phenyl)-3-phenyl-propyl]-isopropyl-amino}-1-phenyl-propyl)-4-methyl-phenol, and/or (3-{2-[2-(3-diisopropylamino-1-phenyl-propyl)-4-methyl-phenoxymetoxy]-5-methyl-phenyl}-3-phenyl-propyl)-diisopropyl-amine, having the following structural formulae Dimer 1:

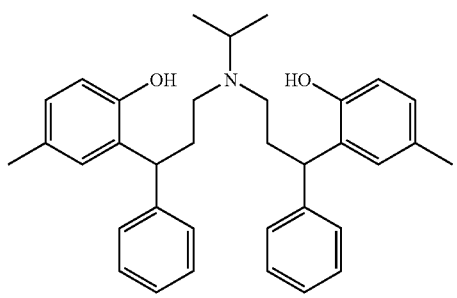

Dimer 2:

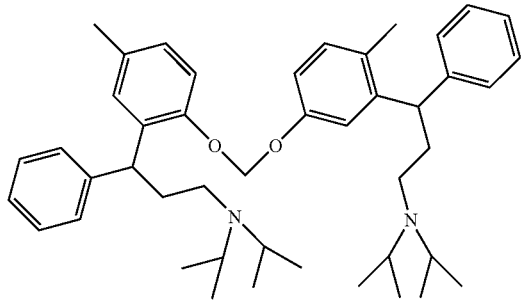

There is a need, therefore, for the provision of improved processes of preparing tolterodine, whereby the above problems encountered by employing prior art techniques can be alleviated and a product with improved purity can be obtained. This is now achieved by the present invention.

SUMMARY OF THE INVENTION

There is now provided by the present invention racemic tolterodine free base in crystalline form, which in turn can allow the preparation of substantially pure (+)tolterodine tartrate. The present invention further provides racemic tolterodine free base in crystalline form containing less than about 0.2% of dimeric impurity. The dimeric impurity associated with tolterodine according to the present invention can be one or both of the following impurities Dimer 1:

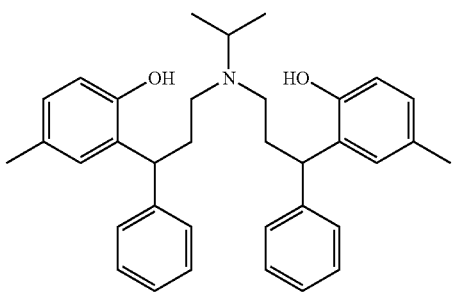

Dimer 2:

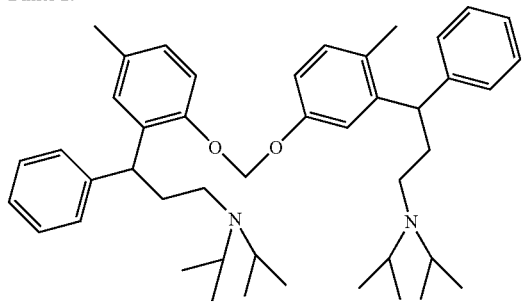

The present invention further provides a process of preparing racemic tolterodine free base in crystalline form, which comprises deprotection of protected intermediate [3-(2-methoxy-5-methyl-phenyl)-3-phenyl-propyl]-diisopropylamine of formula (II)

(II)

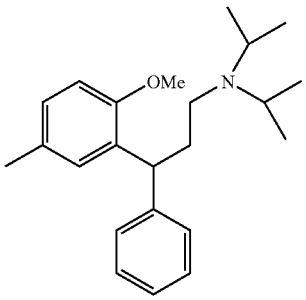

wherein a solvent is present in the reaction mass obtained further to deprotection and is selected so that a substantially mobile reaction mass is achieved at temperatures in the range of 70 to 100° C. Protected intermediate [3-(2-methoxy-5-methyl-phenyl)-3-phenyl-propyl]-diisopropylamine of formula (II) is prepared by techniques known in the art, namely following the reaction scheme given above for U.S. Pat. No. 5,382,600 and substantially as hereinafter described in greater detail in the accompanying Examples.

DETAILED DESCRIPTION OF THE INVENTION

Suitably the deprotection is carried out in the absence of solvent and preferably employs pyridine hydrochloride, typically under an inert atmosphere at elevated temperatures, suitably in the range of 200 to 220° C. Preferably the resulting reaction mass is then cooled to a temperature in the range of 110 to 130° C. and a solvent is added thereto so as to obtain a substantially mobile reaction mass as described above. A preferred solvent is dimethylformamide.

The crude hydrochloride salt of racemic tolterodine present in the resulting reaction mass is then basified, typically employing ammonia, and the resulting racemic tolterodine free base is extracted and precipitated to provide crystalline racemic tolterodine free base. Preferably, the process further comprises a purification step wherein the above obtained racemic tolterodine free base in crystalline form is further dissolved in a selected organic solvent and precipitated to obtain racemic tolterodine free base in crystalline form containing less than about 0.1% of dimeric impurity. A suitable solvent can be an alkane, such as n-hexane.

The present invention further provides, therefore, racemic tolterodine free base in crystalline form prepared by a process substantially as described herein. Preferably, the present invention provides racemic tolterodine free base in crystalline form containing less than about 0.2% of dimeric impurity.

The above process preferably further comprises resolving the thus obtained racemic tolterodine free base to obtain (+)tolterodine tartrate containing less than about 0.1% of dimeric impurity and there is further provided by the present invention (+)tolterodine tartrate prepared by the above process.

According to the present invention racemic tolterodine free base in crystalline form can alternatively be prepared as follows. There is further provided by the present invention, therefore, a process of preparing racemic tolterodine free base in crystalline form, which process comprises deprotection of a benzyl protected intermediate of formula (III)

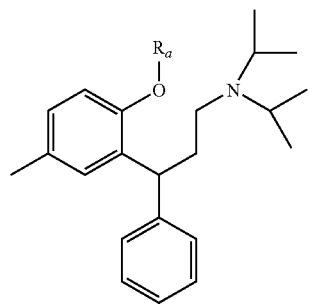

(III)

where $R_a$ can represent unsubstituted benzyl, or may typically represent a suitably substituted benzyl protecting group, such as halo or $C_{1-4}$alkoxy substituted benzyl. The above process may optionally further comprise a further purification step substantially as hereinbefore described and additionally may preferably further comprise resolving the thus obtained racemic tolterodine free base to obtain (+)tolterodine tartrate containing less than about 0.1% of dimeric impurity. The present invention thus further provides racemic tolterodine free base in crystalline form and/or (+)tolterodine tartrate prepared by the above process.

Preferably $R_a$ represents unsubstituted benzyl. Typically, the deprotection employs hydrogenation suitably in the presence of palladium on carbon.

An intermediate compound of formula (III) can suitably be prepared by reaction of diisopropylamine with an intermediate compound of formula (IV)

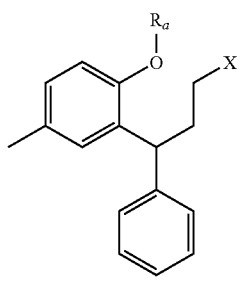

(IV)

where $R_a$ is as defined above and X represents a suitable leaving group, such as an alkyl or arylsulphonyloxy group, preferably tosylate. Typically, the reaction is carried out at a temperature in the range of 90 to 130° C., followed by cooling to room temperature and concentration under vacuum.

An intermediate compound of formula (IV) is suitably prepared from an intermediate compound of formula (V)

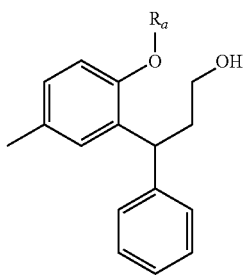

(V)

typically by reaction thereof with an alkyl or aryl sulphonyl halide, such as p-toluene sulphonyl chloride. Suitably, a compound of formula (V) and the sulphonyl halide are dissolved in respective organic solvents, with the reaction typically being carried out in the presence of a base, such as triethyl amine or the like. The sulphonyl halide can be added to a compound of formula (V) over an extended time period at room temperature with stirring. The organic layer is then separated, washed with acid and neutralised with an appropriate base.

Suitably a compound of formula (V) can be prepared by protection of an intermediate compound of formula (VI)

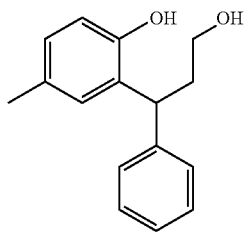

(VI)

by introduction of group $R_a$. Suitably a compound of formula (VI) is dissolved in a suitable organic solvent, such as acetone, and a benzyl halide such as for example, benzyl chloride is added. Suitable bases for this reaction are carbonates or hydroxides of alkali metals, a preferred base being anhydrous potassium carbonate. It is preferable to use a catalyst such as potassium iodide. The reaction mixture is suitably refluxed, subsequently cooled, filtered and concentrated under vacuum.

A compound of formula (VI) can suitably be prepared from 6-methyl-4-phenyl-chroman-2-one, which is known in the art, for example U.S. Pat. No. 5,382,600. Typically, sodium borohydride is added to 6-methyl-4-phenyl-chroman-2-one, followed by stirring. The reaction mixture is then suitably treated with an organic acid, such as acetic acid, followed by concentration under vacuum to yield a compound of formula (VI).

Intermediate compounds of formulae (V) and (VI) represent novel compounds per se and these novel intermediates form further aspects of the present invention.

Tolterodine as provided by the present invention is suitable for use as an anti-cholinergic agent and there is provided by the present invention a pharmaceutical composition comprising tolterodine as provided by the present invention substantially as hereinbefore described, together with a pharmaceutically acceptable carrier, diluent or excipient therefor. In accordance with the invention suitable compositions can be for oral use, for injection, or the like, in accordance with accepted pharmaceutical procedures. Such pharmaceutical compositions comprise tolterodine as provided by the present invention substantially as hereinbefore described in association with compatible pharmaceutically acceptable carrier materials, or diluents, as is well known in the art. The carriers may be any inert material, organic or inorganic, suitable for enteral, percutaneous or parenteral administration such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, and conventional additives such as stabilizers, wetting agents, emulsifiers, flavouring agents, buffers, and the like.

The compositions according to the invention can e.g. be made up in solid or liquid form for oral administration, such as tablets, capsules, powders, syrups, elixirs and the like, in the form of sterile solutions, suspensions or emulsions for parenteral administration, and the like.

There is also provided tolterodine as provided by the present invention substantially as hereinbefore described for use in therapy. The compounds and compositions according to the invention are useful for treating cholinergic disorders, in particular urinary incontinence.

There is further provided by the present invention, therefore, a method of treating a condition prevented, ameliorated or eliminated by the administration of an anti-cholinergic agent, which method comprises administration to the patient a therapeutically effective amount of tolterodine as provided by the present invention substantially as hereinbefore described. In particular, such a method comprises treatment of urinary incontinence by administration of tolterodine as provided by the present invention substantially as hereinbefore described. There is also provided use of tolterodine as provided by the present invention in the manufacture of a medicament for the treatment of urinary incontinence. As is well known, the dosage depends on several factors, such as mode of administration, the age and weight of the patient, the severity of the condition to be treated, and the like. The daily dosage may, for example, be from about 0.05 mg to about 4 mg per kilo of body weight, administered in one or more doses, e.g. containing from about 0.05 to about 200 mg each.

The present invention will now be further limited by the following Intermediates and Examples, which do not limit the scope of the invention in any way.

INTERMEDIATES

Intermediate 1

Synthesis of 6-methyl-4-phenyl-chroman-2-one

Cinnamic acid (100 gms) and p-cresol (76.6 gms) were charged to a clean and dry flask under nitrogen and stirred. Concentrated sulphuric acid was slowly charged and the reaction mixture heated to 125° C.-130° C. for 6 hours. After completion of reaction the mixture was cooled to about 60° C. and about 50 ml water and about 300 ml toluene were charged under stirring. The layers were separated. The toluene layer was washed with aqueous saturated solution of sodium bicarbonate and water. The organic layer was dried over sodium sulfate and concentrated under vacuum, at a temperature below 50° C. The residue was stripped with 2×100 ml IPA. The residue was dissolved in 200 ml isopropanol, chilled to 5° C. and stirred for 2 hours. The solids obtained were filtered and dried at about 60° C. for 4-5 hours to give about 135 to 137 gms of the title product.

Intermediate 2

Synthesis of 3-(2-hydroxy-5-methyl phenyl)-3-phenyl propionic acid methyl ester

Acetone (200 ml) and methanol (200 ml) were taken in a dry flask and 100 gms of Intermediate 1 were charged thereto under stirring. 71 gms of potassium carbonate and 66 ml dimethyl sulphate were charged thereto and the reaction mixture was heated to about 50° C. to 55° C. for 24 hours. After completion of reaction the reaction mass was cooled to room temperature and the inorganics filtered. The clear filtrate was concentrated under vacuum to obtain an oily residue. The residue was dissolved in methylene chloride and the organic layer was washed with water. The organic layer was concentrated under vacuum to obtain the title compound as an oil (117-119 gms).

Intermediate 3

Synthesis of 3-(2-methoxy-5-methyl-phenyl)-3-phenyl-proan-1-ol

THF (200 ml) and 16 gms of sodium borohydride were charged to a clean dry flask under nitrogen. The mixture was cooled to about −10° C. and 100 gms of Intermediate 2 dissolved in 250 ml tetrahydrofuran was added slowly at a temperature in the range of 0° C. to −10° C. over 2-3 hours. 72 ml of boron trifluoride etherate was charged slowly over 3 hours maintaining the temperature between 0° C. to 5° C. After completion of addition, the temperature was slowly raised to between 25° C. to 30° C. and the reaction mass stirred for 2 hours. After completion of reaction, the reaction mixture was cooled to about 5° C. and 3 M hydrochloric acid solution was added slowly to adjust the pH to between 1-3. The reaction mixture was filtered. The clear filtrate was concentrated under vacuum to give the title compound as an oil (95 gms).

Intermediate 4

Synthesis of Toluene-4-sulfonic acid-3-(2-methoxy-5-methyl-phenyl)-3-phenyl propyl ester MDC (200 ml) and Intermediate 3 (100 gms) were charged in a clean dry flask under nitrogen and stirred. 175 ml TEA was added and the reaction mixture cooled to about −5° C. A solution of 190 gms p-toluene sulfonyl chloride in 500 ml MDC was charged slowly over 2 hours at −5° C. to 0° C. The reaction mixture was stirred for 3 hours. After completion of reaction, 250 ml of water was charged below 10° C. The organic layer was separated and washed with 2×150 ml of 2N HCl and finally with 3×200 ml of water. The organic layer was dried and concentrated under vacuum below 45° C. to obtain an oil. The oil was dissolved in a mixture of 100 ml acetone and 600 ml n-hexane and slowly cooled to 5° C. and stirred for 2 hours. The solids were filtered and dried at 50° C. under vacuum for 4 hours to obtain the title compound (135-138 gms).

Intermediate 5

Synthesis of [3-(2-methoxy-5-methyl-phenyl)-3-phenyl-propyl]-diisopropyl amine A mixture of 100 gms of Intermediate 4 and 324 ml of diisopropyl amine in 200 ml of acetonitrile was charged in an autoclave and heated under pressure at 120° C. to 125° C. for 4-5 hours. After completion of reaction, the reaction mixture was cooled to room temperature and concentrated under vacuum below 60° C. to a residue. The residue was dissolved in diisopropyl ether. 60 ml of 2N NaOH was added and the layers separated. The organic layer was then extracted with 3N HCl. The aqueous layer was then basified with 4N NaOH and the product re-extracted into MDC. The organic layer was then dried and concentrated to obtain an oil (65 gms).

Intermediate 6

2-(3-hydroxy-1-phenyl-propyl)-4-methyl-phenol 6-methyl-4-phenyl-chroman-2-one, 250 gins was stirred in 1.25 liters methanol at room temperature. Sodium borohydride 70 gms was added slowly, whilst maintaining the temperature at room temperature. The reaction mixture was stirred for 18 hours. After completion of reaction, the pH of the reaction mass was adjusted to pH 5 using acetic acid. The reaction mixture was concentrated under vacuum and 2 liters of water were added. The reaction mass was stirred for 30 minutes and the solids filtered. The solids were dried at 55° C. in a hot air oven for 20 hours. Weight 248 gms.

Purification: Crude Intermediate I prepared as above was dissolved in 700 ml of toluene and heated to 85° C.-87° C. The clear solution was gradually cooled to room temperature and stirred for 30 minutes. The solids were filtered and washed with toluene. The solids were dried in a hot air oven at 55° C.-60° C. Yield: 222 gms. Mp (117-119° C.)

Intermediate 7

3-(2-benzyloxy-5-methyl-phenyl)-3-phenyl-propan-1-ol

Intermediate 6 (75 gms) was dissolved in 750 ml acetone. Anhydrous potassium carbonate (170 gins) and potassium iodide (0.75 gins) were added. 60 ml of benzyl chloride was added slowly and the reaction mixture was refluxed for 42 hours. The reaction mass was cooled to room temperature and filtered. The acetone was concentrated under vacuum. N-hexane 300 ml was added to the oil and stirred for one hour at 20° C. The product was filtered and the solids were dried at 50° C. to 55° C. in a hot air oven for 3 hours. Yield: 102 gms. (mp 69-71° C.)

Intermediate 8

Toluene-4-sulfonic acid-3-(2-benzyloxy-5-methyl-phenyl)-3-phenyl propyl ester Intermediate 7 (50 gms) was dissolved in 300 ml of methylene chloride. Triethyl amine (45.6 gins) was added. The reaction mixture was cooled to 5° C. and 34.3 gms of p-toluene sulphonyl chloride dissolved in 140 ml methylene chloride was added slowly and the reaction mixture stirred for 18 hours at room temperature. The reaction mixture was quenched with 100 ml water. The organic layer was separated and was washed with 75 ml 2N HCl. The organic layer was washed to neutral pH with 5% sodium bicarbonate solution. The methylene chloride layer was dried over sodium sulphate and concentrated under vacuum to get an oil. Yield: 73 gms.

Intermediate 9

[3-(2-benzyloxy-5-methyl-phenyl)-3-phenyl-propyl]-diisopropyl amine

Intermediate 8 (50 gms) was dissolved in acetonitrile (150 ml). Diisopropyl amine (150 gms) was added and the reaction mass was heated in an autoclave at 100° C.-120° C. for 4 hours. The mass was cooled to room temperature, concentrated under vacuum to remove acetonitrile and 200 ml toluene and 150 ml of water were added. The organic layer was separated, washed with water and concentrated to get oil. Yield: 38 gins.

EXAMPLES

Example 1

[3-(2-hydroxy-5-methyl-phenyl)-3-phenyl-propyl]-diisopropyl amine (Racemic Tolterodine Free Base)

Intermediate 5 (100 gms) and 107 gms of Pyridine HCl were charged under nitrogen to a 2 liter. RB flask. The mixture was heated slowly over 2 hours to a temperature of about 210° C. and maintained for 1.5 hours at that temperature. The reaction mixture was cooled to about 120° C. and 100 ml of dimethylformamide was added slowly. The reaction mixture was further cooled to about 70° C. and quenched into 500 ml of ice water. The mixture was stirred for another 3 hours at about 5° C. The precipitated solids were filtered and washed with chilled water to obtain the title product as a hydrochloride salt.

The crude salt was dissolved in water, basified with liquor ammonia and the racemic tolteridone base was extracted into n-hexane. The hexane layer was separated, dried and concentrated to a volume of about 200 ml. The clear solution was chilled to 0° C.-5° C. and stirred for 3 hours at 0° C. to 5° C. The precipitated solids were filtered and dried below 40° C. under vacuum to give the racemic base of tolterodine –80 gms (HPLC: about 99% purity).

Example 2

Purification of [3-(2-hydroxy-5-methyl-phenyl)-3-phenyl-propyl]-diisopropyl amine (Racemic Tolterodine Free Base)

The crude base (80 gms) obtained according to Example 1 was dissolved in 150 ml n-hexane at about 50° C. The clear solution was cooled to 0° C.-5° C. for 3 hours and the precipitated solids were filtered and dried to give about 70 gms of pure racemic tolterodine base (HPLC>99.8%).

Example 3

S(+)-2-(diisopropylamino-1-phenyl-propyl)-4-methyl phenol tartrate ((+) tolterodine tartrate)

Pure racemic tolterodine free base (70 gms) obtained according to Example 2 was dissolved in 400 ml alcohol. 45 gms of L(+)tartaric acid was added and the mixture was heated to about 50° C. for 30 minutes and cooled to room temperature and stirred for 2 hours. The mixture was further cooled to 10° C. and stirred for one hour. The precipitated solids were filtered and dried to give 75 gms of (+) tolterodine tartrate.

Example 4

S(+)-2-(diisopropylamino-1-phenyl-propyl)-4-methyl phenol tartrate ((+) Tolterodine Tartrate)

Intermediate 9 (35 gns) was dissolved in 150 ml of methanol. 10% w/w palladium on carbon catalyst (3.5 gms) was added and the reaction mass was hydrogenated in an autoclave under 50 psi pressure of hydrogen at 50° C. for 3 hours. After completion of reaction, the catalyst was filtered and the clear filtrate was concentrated under vacuum to get an oil. The residue was dissolved in 100 ml n-hexane. The clear solution was chilled to 0° C. and stirred for 3 hours. The precipitated solids were filtered and dried at room temperature under vacuum to give racemic tolterodine base. The base was dissolved in 200 ml ethanol and 10 gms L(+) tartaric acid was added. The reaction mixture was refluxed for 2 hours and cooled to 25° C. and stirred for 2 hours. The product was filtered and dried under vacuum at 60° C. to give (+)tolterodine tartrate.

Example 5

The dimeric impurity associated with tolterodine tartrate as provided by the present invention was measured by the following HPLC method and substantially as hereinbefore described a dimeric impurity level of less than about 0.1% was measured for tolterodine tartrate as prepared by the present invention.

The analysis was carried out on a Shimadzu H 2010 A equipped with a u.v. detector at 215 nm and Inertsil C18 column 25 cm×4.6 mm with a particle size of 5 μm maintained at 25° C., using a gradient method as described in the table below with a mobile phase consisting of Solution A: Buffer 0.05 M $KH_2PO_4$, pH adjusted to 3.5 with O-phosphoric acid and Solution B: Acetonitrile. The flow rate was maintained at 1.0 ml/minute.

| Time  | Solution A | Solution B |
|-------|------------|------------|
| 0.01  | 65         | 35         |
| 5.00  | 65         | 35         |
| 5.01  | 65         | 35         |
| 20.00 | 50         | 50         |
| 20.01 | 50         | 50         |
| 40.00 | 30         | 70         |
| 40.01 | 65         | 35         |
| 50.00 | 65         | 35         |

| Relative retention Times of Impurities | |
|---|---|
| Des-isopropyl tolterodine | 0.68 |
| Dimer 2 | 1.43 |
| Dimer 1 | 2.39 |

The invention claimed is:

1. Racemic tolterodine free base in crystalline form.

2. Racemic tolterodine free base in crystalline form according to claim 1 containing less than about 0.2% of dimeric impurity.

3. Tolterodine according to claim 2, wherein the dimeric impurity comprises one or both of the following impurities:

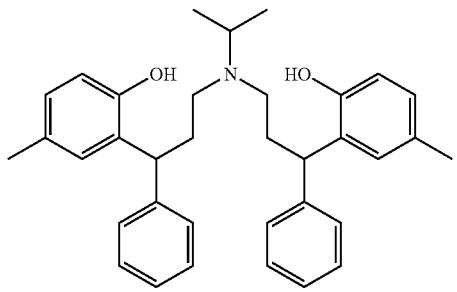
Dimer 1

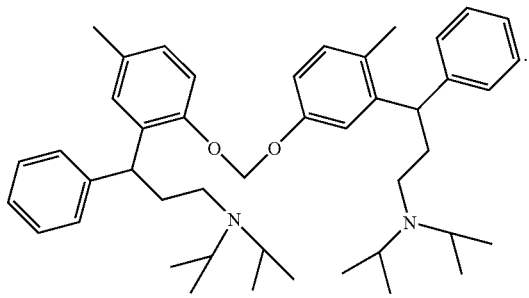
Dimer 2

4. A process of preparing racemic tolterodine free base in crystalline form, which comprises deprotection of protected intermediate of formula (II)

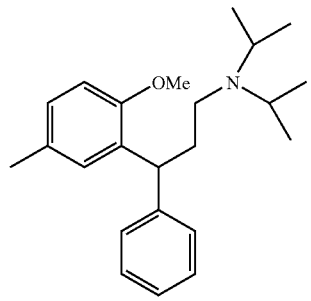
(II)

wherein a solvent is present in the reaction mass obtained further to the deprotection and is selected so that a substantially mobile reaction mass is achieved at temperatures in the range of 70 to 100° C.

5. A process according to claim 4, wherein said deprotection employs pyridine hydrochloride.

6. A process according to claim 5, wherein said deprotection is carried out under an inert atmosphere at a temperature in the range of 200 to 220° C.

7. A process according to claim 6, wherein further to said deprotection said reaction mass is cooled to a temperature in the range of 110 to 130° C. and said solvent is added thereto.

8. A process according to claim 4, wherein said solvent is dimethylformamide.

9. A process according to claim 5, wherein the resulting crude hydrochloride salt of racemic tolterodine is basified and the resulting racemic tolterodine free base extracted and precipitated to provide crystalline racemic tolterodine free base.

10. A process according to claim 9, which further comprises a purification step to obtain racemic tolterodine free base in crystalline form containing less than about 0.2% of dimeric impurity.

11. A process according to claim 10, which further comprises resolving the thus obtained racemic tolterodine free base to obtain (+)tolterodine tartrate containing less than about 0.1% of dimeric impurity.

12. A process according to claim 11, wherein said dimeric impurity comprises one or both of the following impurities:

Dimer 1

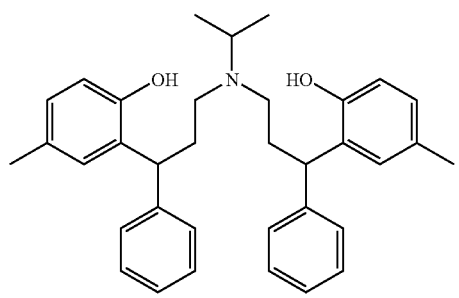

Dimer 2

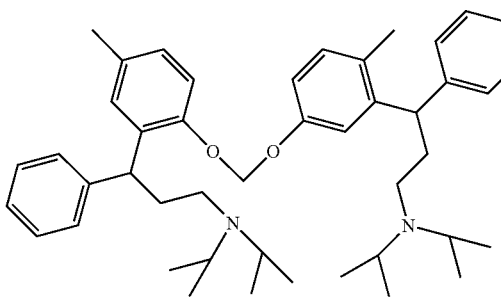

13. A process of preparing racemic tolterodine free base in crystalline form, which process comprises deprotection of a benzyl protected intermediate of formula (III)

(III)

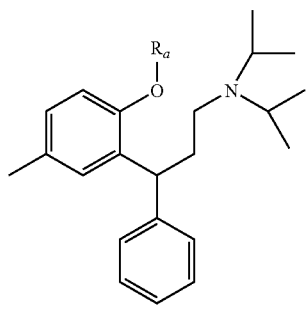

where $R_a$ represents unsubstituted benzyl, or a substituted benzyl protecting group.

14. A process according to claim 13, which further comprises resolving the thus obtained racemic tolterodine free base to obtain (+)tolterodine tartrate containing less than about 0.1% of dimeric impurity.

15. A process according to claim 14, wherein $R_a$ represents unsubstituted benzyl.

16. A process according to claim 13, wherein an intermediate compound of formula (III) is prepared by reaction of diisopropylamine with an intermediate compound of formula (IV)

(IV)

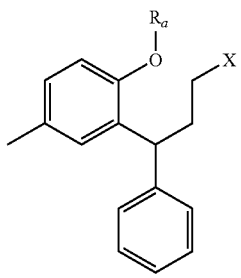

where X represents a leaving group.

17. A process according to claim 16, wherein X represents arylsulphonyloxy.

18. A process according to claim 17, wherein X represents tosylate.

19. A process according to claim 16, wherein an intermediate compound of formula (IV) is prepared from an intermediate compound of formula (V)

(V)

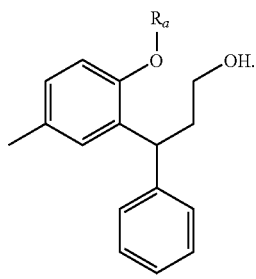

20. A process according to claim 19, wherein a compound of formula (V) is prepared by protection of an intermediate compound of formula (VI)

(VI)

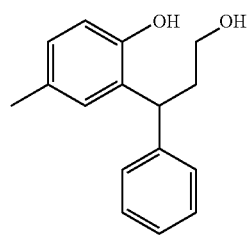

by introduction of group $R_a$.

21. A process according to claim 20, wherein a compound of formula (VI) is prepared from 6-methyl-4-phenyl-chroman-2-one.

22. An intermediate compound of formula (V) or (VI):

(V)

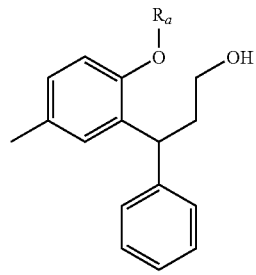

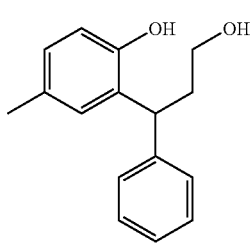
where $R_a$ represents unsubstituted benzyl, or a substituted benzyl protecting group.
23. An intermediate of formula (V) according to claim 22, wherein $R_a$ represents unsubstituted benzyl.
24. A pharmaceutical composition comprising tolterodine according to claim 1, together with a pharmaceutically acceptable carrier, diluent or excipient therefor.
\* \* \* \* \*